United States Patent

Ohayon

[11] Patent Number: 5,810,253
[45] Date of Patent: *Sep. 22, 1998

[54] DEVICE FOR THE CONTROLLED DISPENSATION AND EVAPORATION OF VOLATILE LIQUIDS

[76] Inventor: Nissim Ohayon, 4 Simtat Hashoshana, Mevaseret Zion, Israel, 90805

[*] Notice: The term of this patent shall not extend beyond the expiration date of Pat. No. 5,400,973.

[21] Appl. No.: 626,191

[22] Filed: Mar. 29, 1996

[30] Foreign Application Priority Data

Jul. 24, 1995 [IL] Israel ....................................... 114 716

[51] Int. Cl.⁶ ................................................... A24F 25/00
[52] U.S. Cl. .................................. 239/43; 239/56; 239/58
[58] Field of Search ................................. 239/43, 58, 56, 239/37, 38, 47, 59

[56] References Cited

U.S. PATENT DOCUMENTS

| | | | |
|---|---|---|---|
| 542,376 | 7/1895 | Bradshaw | 239/43 |
| 746,453 | 12/1903 | Vondian | 239/37 X |
| 976,992 | 11/1910 | Effanfin | 239/43 |
| 1,164,624 | 12/1915 | Appleton | 239/433 |
| 1,222,756 | 4/1917 | Grinen | 239/43 |
| 2,481,296 | 9/1949 | Dupuy | 239/59 X |
| 2,991,577 | 7/1961 | Dundy | 239/43 X |
| 4,200,229 | 4/1980 | Spector . | |
| 4,247,042 | 1/1981 | Schimanski et al. . | |
| 4,526,320 | 7/1985 | von Phillipp et al. . | |
| 4,615,486 | 10/1986 | Konicek . | |
| 4,619,383 | 10/1986 | Konicek . | |
| 4,632,310 | 12/1986 | Konicek . | |
| 4,762,275 | 8/1988 | Herbert et al. . | |
| 4,878,615 | 11/1989 | Losi . | |
| 4,917,301 | 4/1990 | Munteanu . | |
| 4,948,047 | 8/1990 | Zembrodt . | |
| 4,995,555 | 2/1991 | Woodruff . | |
| 5,172,859 | 12/1992 | Paglin et al. . | |
| 5,238,187 | 8/1993 | Zlotnik et al. . | |
| 5,324,490 | 6/1994 | Van Vlahakis et al. | 239/60 X |

FOREIGN PATENT DOCUMENTS

| | | |
|---|---|---|
| 0078114 | 10/1982 | European Pat. Off. . |
| 0497710 | 3/1992 | European Pat. Off. . |
| 2629559 | 4/1988 | France . |
| 8924602 | 11/1989 | France . |
| 2228681 | 9/1990 | United Kingdom . |
| 8800125 | 4/1988 | WIPO . |
| 9000798 | 11/1990 | WIPO . |

*Primary Examiner*—Kevin Weldon
*Attorney, Agent, or Firm*—Reising, Ethington, Learman & McCulloch, PLLC

[57] ABSTRACT

A device for the controlled dispensation and unattended evaporation of volatile liquids includes a housing that accommodates a reservoir charged with a volatile liquid. The reservoir has an outlet for releasing the volatile liquid from a lower end of the reservoir. A valve mounted on the reservoir controls the flow of the volatile liquid through the reservoir outlet. The valve allows a controlled quantity of the volatile liquid, in the form of discrete droplets, to be gravitationally delivered, on demand, to an absorbent matrix. A matrix housing supports the matrix below the reservoir outlet. The absorbent matrix absorbs volatile liquid that the outlet delivers and dispenses the volatile liquid as a vapor to an external environment. The absorbent matrix dispenses the vapor via a ventilator that may be either releasably or integrally mounted to either the matrix housing or the housing that accommodates the reservoir.

27 Claims, 10 Drawing Sheets

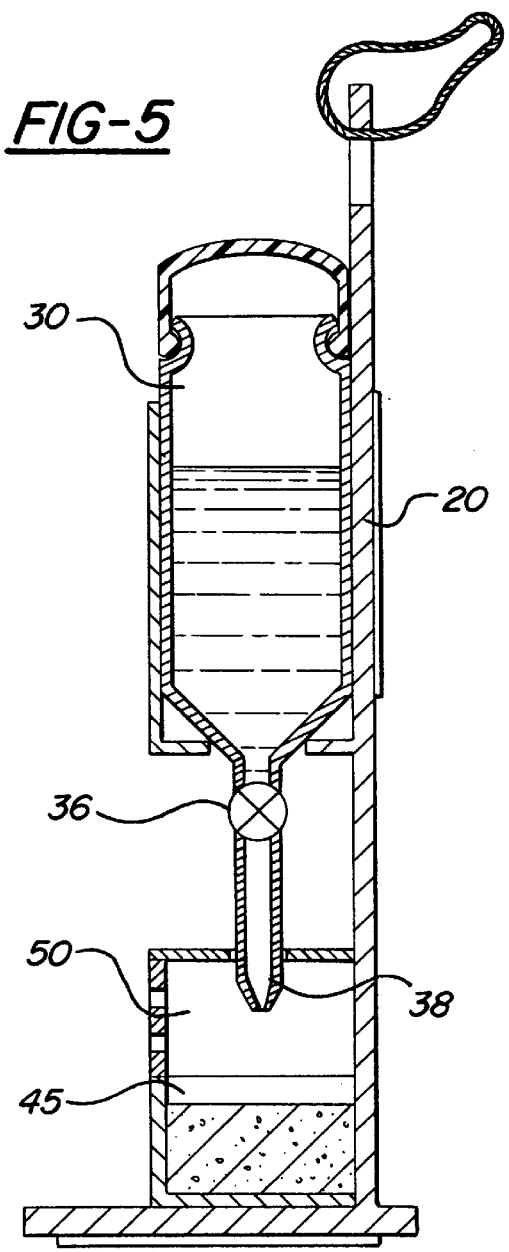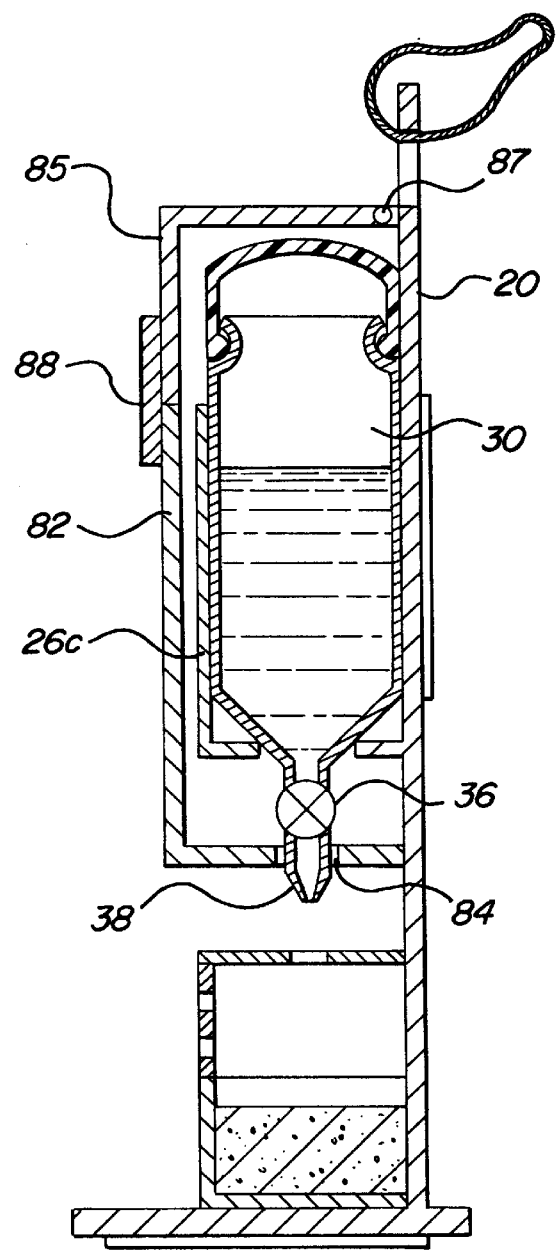

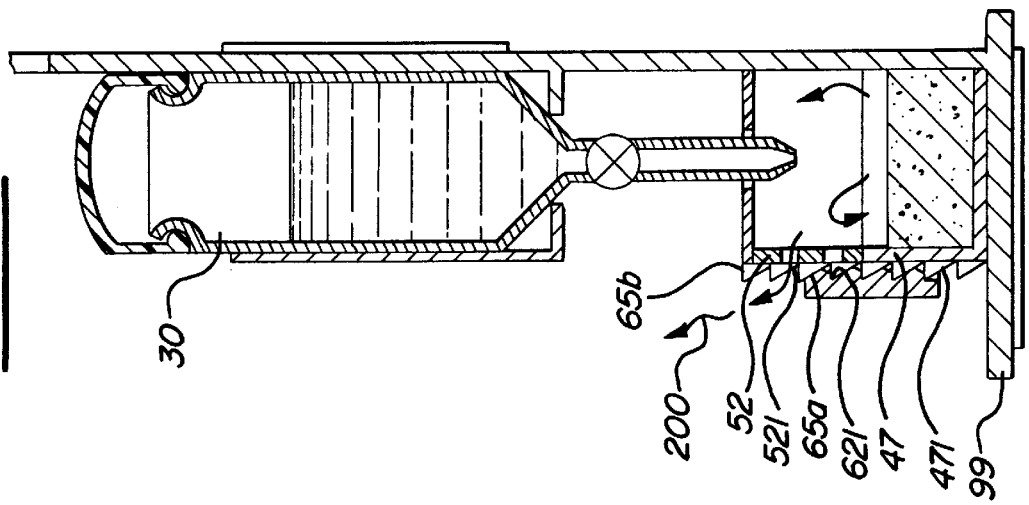
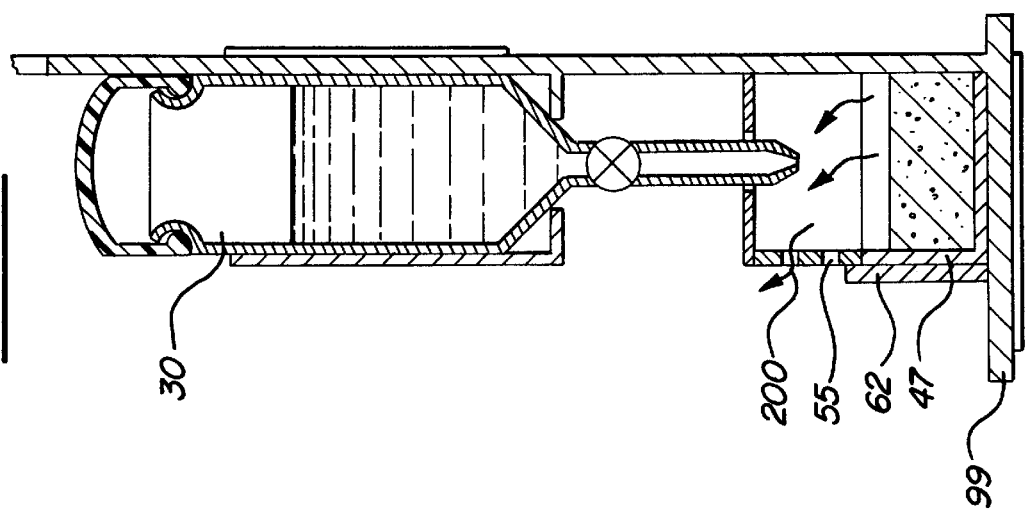
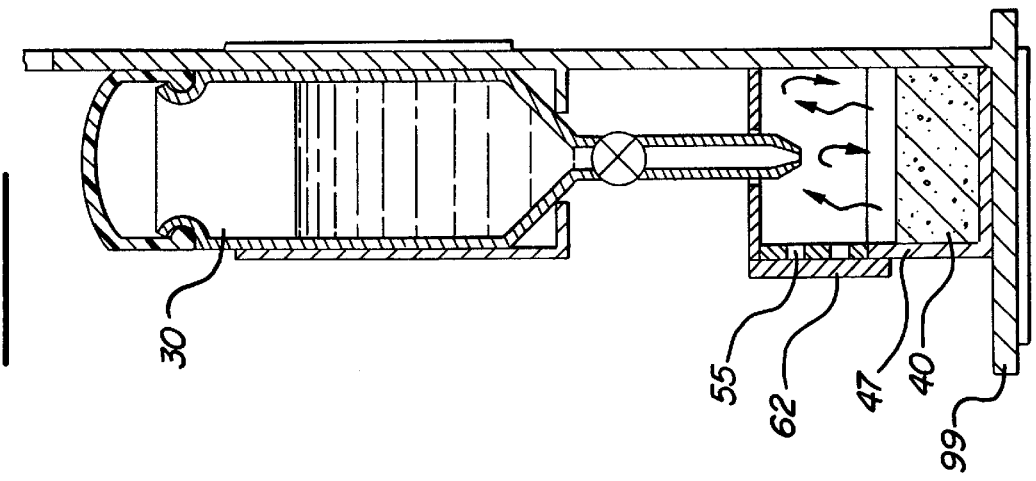

DEVICE FOR THE CONTROLLED DISPENSATION AND EVAPORATION OF VOLATILE LIQUIDS

INTRODUCTION

The present ivention relates to the dispensing of volatile liquids as vapours, in particular to the controlled dispensation and unattended release of volatile liquids including essential oils, plant extracts, air-freshening preparations, air purifying preparations, perfumed preparations, smoke neutralising preparations, insect repelling preparations and the like.

There are instances wherein it is necessary or advantageous to be able to dispense a volatile liquid as a vapour for an extended period, and then to suspend dispensation of same till a later date, this procedure being repeatable numerous times on demand. Examples of such instances include the dispensation of air freshener in a lavatory, dispensation of insect repellent in a bedroom during the night, dispensation of smoke neutralising preparations in an office during office hours. On-demand devices like aerosol sprays, for example, while affording the advantage of minimising wastage in that vapour is only released when the device is actuated, are nevertheless unsuitable, since the effects of the vapour, thus delivered are usually very short-term. Devices comprising a reservoir of volatile liquid wherein the same is dispensed onto an absorbent medium have the advantage that vapour may be dispensed continuously from the absorbent medium until the liquid is used up, and many such devices are described in the prior art. However, these devices do not provide an adequate level of control over the rate of dispensation of the liquid coupled with simplicity and versatility of design, and economic use of the contents of the reservoir. In particular, these devices are inadequate to the task of dispensing small amounts of concentrated volatile liquids for subsequent evaporation which may be particularly advantageous for compact dispensing devices. The ability to control the rate of dispensation of the liquid onto an absorbent medium is particularly significant as this ultimately determines how much vapour is to be released, for how long and whether the device may be operated during some periods while being inactive during other periods, on demand. Full and economic utilisation of the liquid is ideal, and is particularly important when highly concentrated liquids are to be dispensed, and this may be achieved in a relatively simple manner by dispensing the liquid under gravity. Simplicity in the design and use of such a device reduces manufacturing costs and enhances marketability.

There are, for example, known gravity fed devices wherein the dispensation of a volatile liquid onto an absorbent medium is initiated by means of a piercing tool which in one operation pierces the reservoir containing the liquid and allows same to flow onto said absorbent medium under gravity, as disclosed in U.S. Pat. Nos. 4,995,555, 4,247,042 and 5,238,187 and also European Pat. Application No. 0078114. However, none of these devices enable the dispensation rate of the liquid to be controlled or even stopped to be subsequently restarted. To an extent, U.S. Pat. Nos. 4,526,320 and 4,762,275 and also UK Patent No. 2,228,681 each disclose devices having some measure of control over the dispensation of liquid insofar as liquid is contained in at least two sub-reservoirs in each device, wherein each sub-reservoir may be opened independently. However, once opened, each sub-reservoir does not allow the user further control over the rate of dispensation of the liquid therein.

WO 91/06212, for example, discloses a device which, while enabling liquid to be dispensed to an absorbent medium at periodic intervals chosen by the user, nevertheless does not allow evaporation of the liquid from the absorbent medium to occur except while liquid is being actively dispensed to the same, nor does it enable fine metering of the dispensed volume of liquid to be effected.

U.S. Pat. No. 5,172,859 discloses an inverted bottle supported within a skirted dish having a pool of liquid at the bottom, and further comprises means for closing the bottle in situ, thereby preventing further dispensation of liquid, while allowing the pool of liquid to evaporate by means of an absorbent medium which sits on the pool. However, the pool of liquid which is already dispensed is disadvantageously vulnerable to spillage, and fine metering of the liquid dispensed to the absorbent medium is not possible. Furthermore, though refilling the bottle may be possible, the configuration of the device does not allow this to be performed in a simple manner.

U.S. Pat. No. 4,878,615 discloses a non gravity fed device which enables liquid to be periodically dispensed onto an absorbent medium via a complex arrangement requiring an auxiliary reservoir as well as a main reservoir, which are coupled together by means of a feedpipe, said arrangement in normal use being particularly unsuitable for permitting the full utilisation of the reservoir contents nor for the economic dispensation of small amounts of a concentrated liquid.

U.S. Pat. No. 4,200,229 also discloses a non gravity fed device, wherein a cartridge, having a bottle, a pump and an absorbent medium, is horizontally insertable into a holder. Disadvantageously, the device would normally require the whole cartridge to be replaced when only the absorbent pad required replacing, and this configuration also enables the unauthorised removal of the cartridge from the holder to be effected with relative ease. In particular, the horizontal orientation of the device, coupled with the use of a feedpipe mounted to the pump and extending into the bottle, renders the device unsuitable for fully utilising the liquid contents during normal use, since it cannot be ensured that the free end of the feedpipe will remain immersed in the said liquid, especially when the level of contents in the bottle diminishes.

None of the above publications describe a gravity fed device comprising a housing having a reservoir charged with liquid and having an outlet at the lower end thereof wherein to ensure economic and full utilisation of the liquid contents therein, and valve means to fully control the flow rate of liquid, including providing for the dispensation of droplets of a concentrated liquid, whereby the liquid is gravitationally dispensed onto an absorbent medium which is in open communication with ventilation means, which is furthermore releasably mounted to the device permitting access to the absorbent medium, and which enables the unattended release of vapour therefrom.

The present invention thus relates particularly to an improvement in vapour dispensing devices, wherein the improvement lies in that the device enables unattended release of vapour for limited pre-programmed periods on demand, while at the same time preventing wastage of the liquid contents when further release of vapour is not required, by enabling the amount of liquid to be dispensed to be substantially fully controlled and providing the economy of full utilisation of the liquid in the device.

The dispensation of small and precise amounts of liquid, such as droplets of a volatile liquid for example, is often necessary. Though there are known devices comprising bottle stoppers which allow liquid to be dispensed in a dropwise manner, it is not possible to control the amount of droplets which are dispensed other than by inverting the bottle to initiate dispensation, and by righting the bottle to terminate same. It is sometimes necessary to dispense a prescribed number of droplets of liquid, for example of concentrated volatile liquid from a bottle onto an absorbent medium for subsequent evaporation therefrom, wherein the ability to control the dispensation of liquid in droplet form in a simple manner would be advantageous. There are many known valve configurations and mechanisms in the art, wherein the flow of liquid from upstream to downstream of the valve may be controlled, though none discloses the ability to control the gravitational dispensation of liquid in a dropwise manner, coupled with a simplicity of design which renders the same viable for use in, for example, in a vapour dispensing device. Thus, this invention also relates to an improvement in valve mechanisms wherein the improvement lies in that the valve enables the throughflow of liquid to be controlled to enable the dispensation of same to be effected in droplet form, whereby actuation of the valve is by means of a simple action.

An object of the present invention is to provide a device for the controlled dispensation and unattended evaporation of volatile liquids, comprising a housing accommodating:

(i) a reservoir charged with said volatile liquid and having an outlet at a lower end thereof;

(ii) valve means suitably mounted on said reservoir for controlling the flow of said volatile liquid through said outlet, wherein said valve means allows a controlled quantity of said volatile liquid to be gravitationally delivered, on demand, to (iii) an absorbent matrix supported by a matrix housing, wherein liquid delivered via said outlet is absorbed into said absorbent matrix and dispensed as a vapour to an external environment; via (iv) ventilation means comprising at least one ventilation opening in open communication with said absorbent matrix and said external environment, wherein said ventilation means may be releasably or integrally mounted to said housing and/or to said matrix housing.

Another object of the present invention is to provide a device for the controlled dispensation and unattended evaporation of volatile liquids which does not adversely affect the ozone layer, and which is not dangerous to dispose of.

Another object of the present invention is to provide a device for the controlled dispensation and unattended evaporation of volatile liquids wherein the reservoir and/or the reservoir contents and/or the absorbent matrix may be easily replaced.

Another object of the present invention is to provide a device for the controlled dispensation and unattended evaporation of volatile liquids wherein concentrated liquids may be dispensed in a dropwise manner.

Another object of the present invention is to provide a device for the controlled dispensation and unattended evaporation of volatile liquids wherein unauthorised tampering and use of the device is substantially prevented.

Another object of the present invention is to provide valve means which enable a liquid to be dispensed in a dropwise manner.

Another object of the present invention is to provide a valve mechanism for controlling the gravitational dispensation of a liquid in droplet form comprising:

(a) a valve casing open at one end thereof and comprising a longitudinal bore, an upper transverse inlet bore having a first diameter and a lower outlet bore generally opposed thereto and having a second diameter, said inlet and outlet bores being in open communication with said longitudinal bore;

(b) a longitudinal plunger comprising a generally transverse bore having a third diameter, wherein said transverse bore comprises an inlet and an outlet, and wherein said plunger is longitudinally insertable in said casing, via said open end and is longitudinally shiftable in, or rotatable within, said casing between an open position, wherein said plunger bore inlet and outlet are respectively aligned with respect to said casing inlet and outlet bores, and a closed position, wherein said plunger bore inlet and outlet are respectively misaligned with respect to said casing inlet and outlet bores; and (c) an annular plug having a bore of said third diameter and sealingly fitted within said upper boss bore, and protruding into the casing bore to form tangential contact with said plunger;

Wherein said valve is characterised in that said third diameter is smaller that said first diameter and said second diameter, and that said third diameter is further correlated to a characteristic droplet size of said liquid, so that in the open position, liquid contained upstream of said plug may be gravitationally dispensed via said plug and plunger bore in discrete droplets into the outlet bore, and further characterised in that in the closed position, the plunger substantially seals the plug core substantially preventing leakage of said liquid therefrom.

To the extent that any of the forgoing patents are relevant to the present invention, they are hereby incorporated in their entirety by reference.

SUMMARY OF THE INVENTION

A device for the controlled dispensation and unattended evaporation of volatile liquids comprises a housing accommodating a reservoir charged with a volatile liquid. The reservoir has an outlet at a lower end of the reservoir. A valve means is suitably mounted on the reservoir to control the flow of the volatile liquid through the outlet. The valve means allows a controlled quantity of the volatile liquid comprising discrete droplets to be gravitationally delivered, on demand, to an absorbent matrix supported by a matrix housing. Liquid delivered via the outlet is absorbed into the absorbent matrix and is dispensed as a vapor to an external environment. The matrix dispenses the vapor via ventilation means comprising at least one ventilation opening in open communication with the absorbent matrix and the external environment.

The present invention differs from the prior art in that it includes a valve means that an operator may predictably and repeatably set to dispense small and precise amounts of volatile liquids in a series of one or more discrete droplets. The valve means therefore precludes the need to incorporate structures and/or processes to deal with excess quantities of the volatile liquid that could otherwise over-saturate and/or flow out of the matrix.

DESCRIPTION OF FIGURES

FIG. 5 shows in side sectional view another embodiment of the invention.

FIG. 6 shows an example of closure means and an example of closure regulating means for a preferred embodiment of the present invention.

FIG. 7 shows an example of security means relating to an embodiment of the present invention.

DESCRIPTION

The present invention relates to a device for the controlled dispensation and unattended evaporation of volatile liquids, comprising a housing accommodating:

(i) a reservoir charged with said volatile liquid and having an outlet at a lower end thereof;

(ii) valve means suitably mounted on said reservoir for controlling the flow of said volatile liquid through said outlet, wherein said valve means allows a controlled quantity of said volatile liquid to be gravitationally delivered, on demand, to (iii) an absorbent matrix supported by a matrix housing, wherein liquid delivered via said outlet is absorbed into said absorbent matrix and dispensed as a vapour to an external environment; via (iv) ventilation means comprising at least one ventilation opening in open communication with said absorbent matrix and said external environment, wherein said ventilation means may be releasably or integrally mounted to said housing and/or to said matrix housing.

The invention will be better understood from a number of embodiments thereof with reference to the appended figures, beginning with a description of each component of each embodiment.

Figure 1:
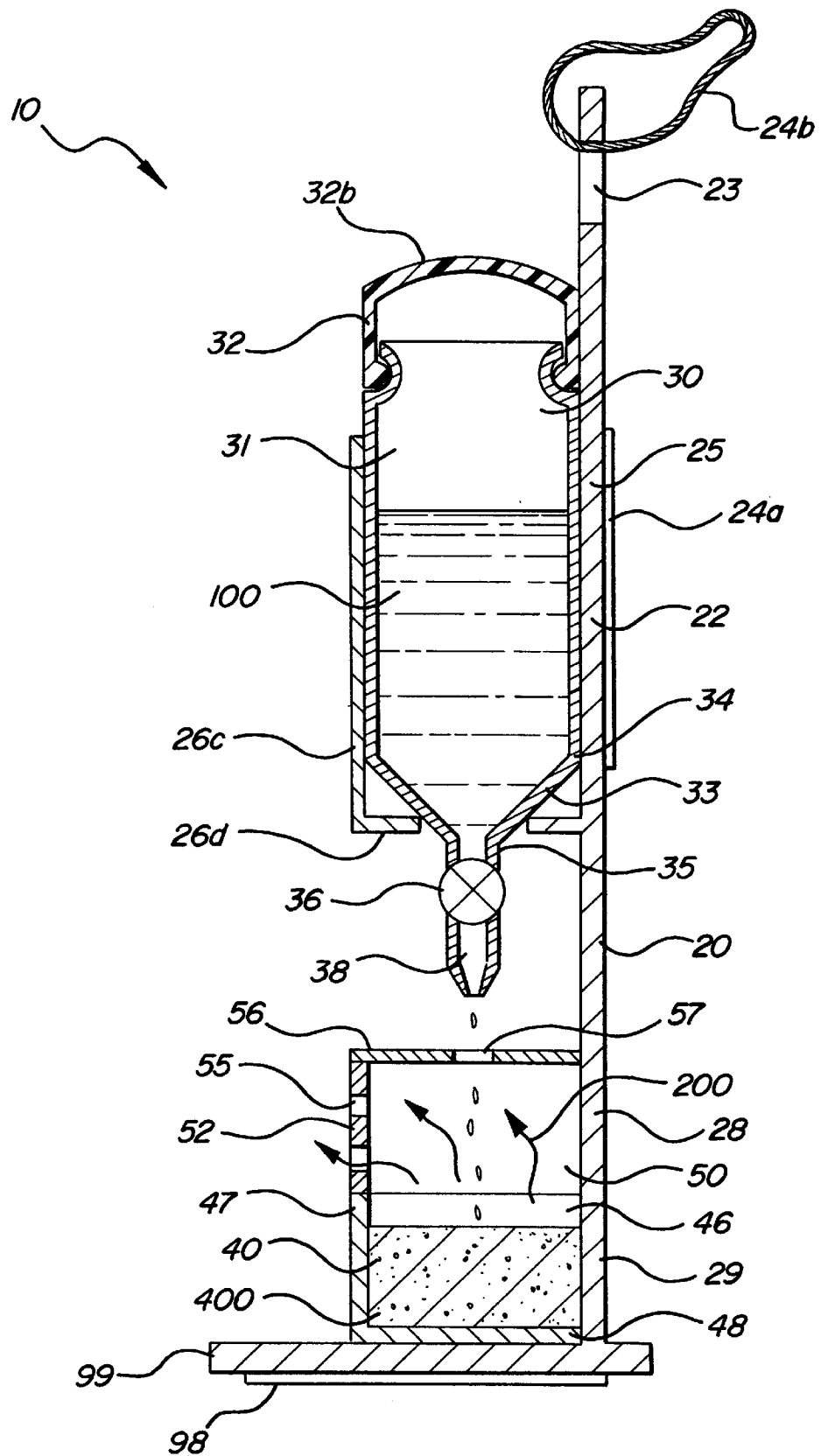
FIG. 1 shows, in side sectional view, a preferred embodiment of the present invention.
Figure 2:
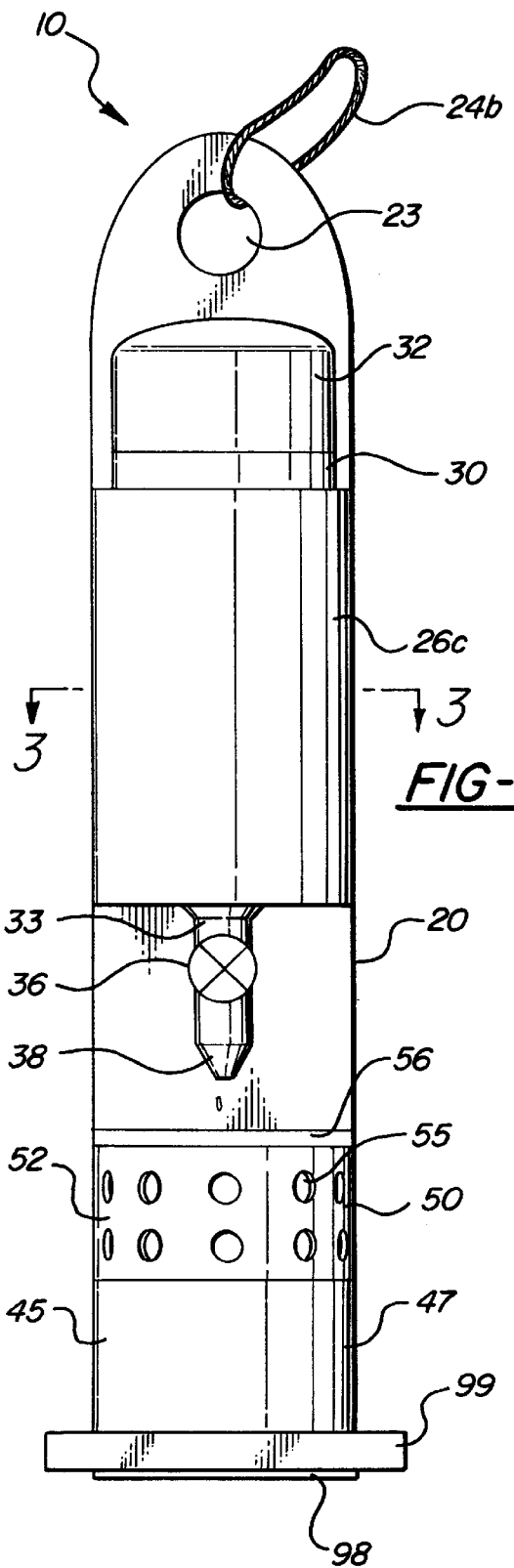
FIG. 2 shows, in front view, the device shown in FIG. 1.
Figure 3:
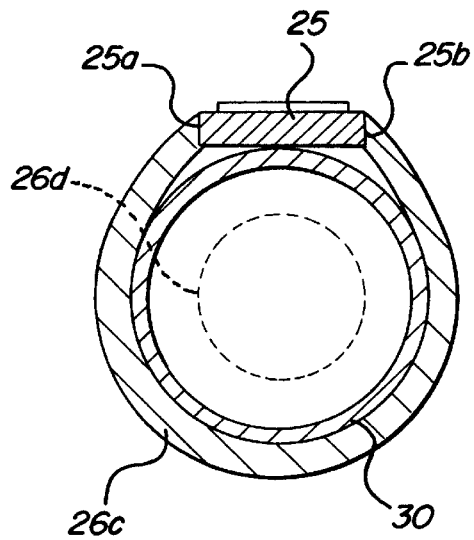
FIG. 3 shows a plan cross-sectional view of the device shown in FIG. 1, taken along X—X.

As illustrated in FIGS. 1, 2 and 3, a preferred embodiment of the device, generally designated (10), comprises a housing (20), accommodating a reservoir (30), an absorbent matrix (40) and ventilation means (50).

Optionally, said device (10) comprises means for releasably or permanently attaching said device to a vertical surface and/or means for hanging said device (10). Thus, said housing (20) typically comprises a vertical flat base part (22) with vertical attachment means (24) for attaching the device (10) to any suitable location where it is required. Said vertical attachment means (24) may comprise a strip (24a) having adhesion means, e.g., an adhesive strip or a magnetic strip, located at the back of the said base part (22), and said strip (24a) enables the device (10) to be releasably or permanently fixed on a suitable wall or any suitable substantially planar vertical surface. Alternatively, or additionally, said vertical attachment means (24) may comprise a length of string or chain (24b) or other suitable material, looped around a suitable orifice (23) located at the uppermost point of the base part (22), although the looped string (24b) may be located at any other suitable location on the device (10). The said looped string (24b) enables the device to be hung from any suitable hanging point, for example a wall hook or a rear-view mirror in a vehicle. Alternatively, the orifice (23) may itself be used to screw the device (10) directly onto a wall, for example, and the device may comprise more than one such orifice (23) for this purpose at suitable locations on the housing (20), for example. Alternatively, the device (10) directly onto a suitable hanging point such as a wall hook by means of the said orifice (23).

In the preferred embodiment, the housing (20) further comprises a horizontal base part (99), which enables the said device (10) to be placed on any substantially planar horizontal surface. Optionally, said base part (99) further comprises suitable attachment means (98), e.g. an adhesive or magnetic strip, for attach the base part (99), either releasably or permanently, to any suitable substantially planar horizontal surface.

The housing may further comprise at least one angled and/or contoured surface comprising said attachment means (98), enabling said device (10) to be releasably or permanently attached to a surface which is correspondingly angled and/or contoured, thus ensuring that the reservoir outlet (38) always remains substantially above the said absorbent matrix (40).

Figure 4:
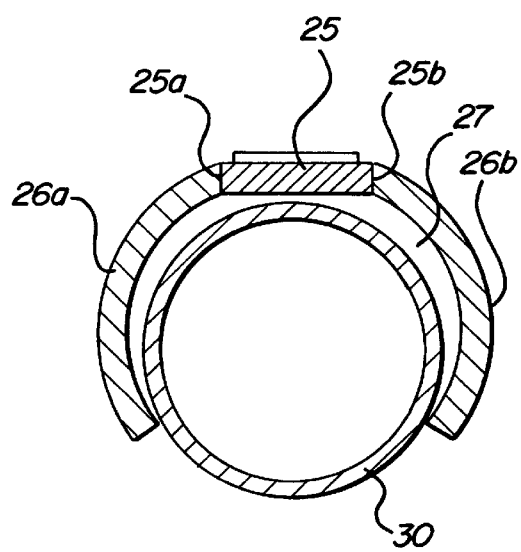
FIG. 4 shows a plan cross-sectional view of another embodiment of the device shown in FIG. 1, taken along X—X.
Figure 8:
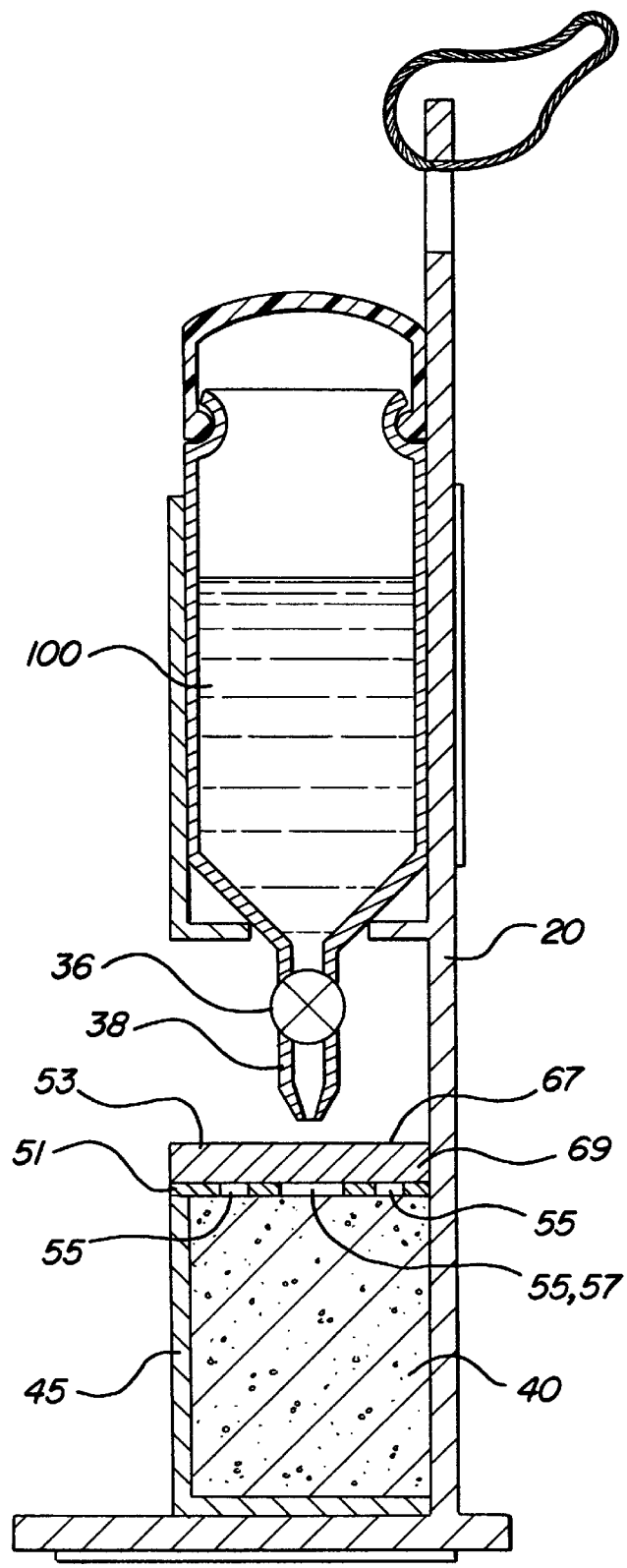
FIG. 8 shows, in side sectional view, another embodiment of the present invention, illustrating another example of ventilation means.

The said housing (20) further comprises suitable mounting means (26) for mounting the said reservoir (30) onto the upper portion (25) of the said base part (22). Said mounting means (26) may comprise preferably metal or plastic clips to hold said reservoir in place. In one embodiment, mounting means (26) comprise two suitably shaped housing walls (26a) and (26b), generally following the external shape of the said reservoir (30), and which are releasably or integrally mounted onto either vertical edges, (25a) and (25b) respectively, of the said upper section (25) of the base part (22), as illustrated in FIG. 4. Said walls (26a) and (26b) together with the said upper section (25) define an internal space (27) to accommodate said reservoir (30). In the preferred embodiment, said internal space (27) may be defined by one continuous wall (26c) attached to either vertical edges (25a) and (25b) of the said upper section (25), as illustrated in FIG. 3. The shape of said continuous wall (26c) is suitably contoured to accommodate the reservoir (30), and is typically substantially cylindrical or semi-cylindrical. Said reservoir (30) may be held firmly in place by lateral pressure from the said walls, (26a) and (26b), or (26c), or may additionally or alternatively rest on a horizontal ledge (26d) provided at the lower ends of said walls, said ledge (26d) facing the said internal space (27).

In the preferred embodiment, said reservoir (30) typically comprises a substantially cylindrical body (31) sealingly capped at the upper end thereof by an integral or separate cap member (32), and comprising a preferably frustaconical lower section (33) sealingly connected at its upper large end (34) to the lower end of said cylindrical body (31), and comprising at its lower narrower end (35) a valve mechanism (36) onto which is connected a suitable nozzle or outlet (38). Alternatively, said reservoir (30) may be of any other suitable shape which may fit into the said mounting means (26) of the said housing (20).

Said reservoir (30) stores the liquid (100) that it is to be dispensed ultimately as a vapour (200). Said liquid (100) may constitute any suitable volatile liquid including air-freshening preparations, air purifying preparations, perfumed preparations, smoke neutralising preparations, and/or insect repelling preparations. Furthermore, said volatile liquid (100) is preferably derived from natural substances including essential oils and/or plant extracts, and is preferably not harmful to people, household pets nor to the environment.

Said reservoir (30) may be a non-refillable, disposable container, or alternatively may be a refillable container. Furthermore, said reservoir (30) is liquid impermeable, and chemically and physically inert with respect to the liquid contents (100) that are stored therein. Said reservoir (30) may be rigid or semi-rigid. Furthermore, said reservoir (30) may be made from any suitable material including metal, plastic, rubber and silicone rubber. Preferably, said reservoir (30) is made from a suitable transparent material, for example a transparent rigid or semi-rigid plastic, enabling the level of liquid contents therein to be continually monitored. In a preferred embodiment, said reservoir (30) is made from glass. Alternatively, said reservoir may be a commercially available container containing said volatile liquid (100).

Alternatively, the said reservoir (30) may be integrally or releasably mounted on said housing (20). Further, said reservoir (30) may be refillable with liquid (100), and may be refilled by removing a releasably mounted cap (32a) at the top thereof, charging the said integral reservoir with liquid contents (100), and replacing the said cap (32a). Thus the cap (32a) may be mounted to the reservoir (30) by any suitable mounting means that allows its removal for filling said reservoir. Said mounting means are known in the art and may include a bayonet fit, interengageable screw threads on facing cylindrical surfaces of the cap and reservoir, or constitute a tight-fitting arrangement between the cap and reservoir.

As hereinbefore described, in the preferred embodiment of the present invention, the said reservoir (30) comprises a suitable valve mechanism (36) mounted onto the lower end (35) thereof. Said valve mechanism (36) can be used to control the flow of liquid contents (100) out of the reservoir (30). In one embodiment, the valve (36) opens on actuation, allowing liquid (100) to be dispensed gravitationally until the valve (36) is subsequently de-actuated, when dispensation of liquid contents (100) is terminated (so long as there remains liquid (100) in the reservoir). Preferably, the valve (36) is spring-loaded, or has an equivalent mechanism, so that the valve (36) de-actuates automatically whenever the same is not being actively actuated. Alternatively, the valve may comprise a regulating mechanism so that liquid contents (100) may be dispensed at a particular rate for a set period of time, or until actively deactuated by the user.

In the preferred embodiment, the valve (36) may be actuated indirectly and set to open following a pre-determined buildup of pressure inside the reservoir (30), and close when internal and external pressures are equalised, and this type of valve is well-known in the art. Pressure may be increased in a reservoir (30) made from a semi-rigid material by squeezing the same, when the release of some of the liquid contents (100) will equalise the pressure inside the reservoir (30) relative to the external ambient atmospheric pressure. The reservoir walls are preferably made from a sufficiently pliant and flexible material, so that when the "squeezing action" is terminated, the reservoir assumes its original shape. Preferably, the valve (36) should also allow air to be sucked into the reservoir on reflux, and thus equalise internal and external pressures, ready for subsequent dispensation of liquid contents (100). If the reservoir (30) is made from a rigid material, pressure therein may be increased by a number of different ways known in the art including, e.g., a pump mechanism. Alternatively, the reservoir cap (32) may be made from a flexible material, such as a rubber bulb (32x) for example, and a squeezing action on the same reduces the volume inside the reservoir (30) thereby increasing the pressure therein, and leading to the dispensation of the said liquid contents (100).

Optionally, said device further comprises means for substantially preventing unauthorised use of said device. Thus, the device (10) may further comprise security means (80), wherein said security means (80) substantially prevents unauthorised use—especially by children—of the said device (10), including actuation of said valve (36), and/or refilling and/or replacing said reservoir (30). Thus in one embodiment, said security means (80) comprises a cover member (82) suitably mounted onto said housing (20), wherein said cover member (82) substantially encloses the reservoir (30) and valve (36), as illustrated in FIG. 7. Said cover member comprises a lower aperture (84), through which said outlet (38) may protrude. If said valve (36) is actuated indirectly, e.g. by a buildup of reservoir internal pressure, as hereinbefore described, the valve (36) may also protrude through said lower aperture (84). Said cover member (82) further comprises means for replacing and/or refilling the said reservoir (30), and for actuating, directly or indirectly, said valve (30). In one embodiment, said cover member (84) comprises a door member (86) suitably dimensioned to permit access to said reservoir (30) and/or valve (36). Said door member (84) may be hinged, or may be detachable, and may further comprise locking means (88), wherein said locking means (88) may comprise a child-proof lock, or alternatively any lock known in the art for substantially preventing unauthorised opening of same. In the preferred embodiment, said security means (80) comprises a second cap member (85), comprising a hinge (87) whereby said second cap member (85) is suitably mounted onto said housing (20), and further comprising locking means (88). In the closed and locked position, said second cap member (85) sealingly fits over the housing (82), denying access to said reservoir (30). Alternatively, continuous wall (26c) may also serve as a cover member, wherein second cap member (85) sealingly fits over same, denying access to said reservoir (30) until said second cap member (85) is opened. Rotation of said second cap member (85) by, say, 90° about the axis of the hinge (87), allows the first cap member (32) to be squeezed in order to increase pressure in the reservoir and indirectly actuate the valve (36), and furthermore allows refilling and/or replacing of the said reservoir (30).

The housing (20) further comprises an absorbent matrix (40) located below the said reservoir (30). Liquid contents (100) from the reservoir (30) which are dispensed by the actuation of valve (36) fall under gravity into the said absorbent matrix (40), which holds the said liquid contents (100) and slowly releases the same in vapour form (200) into the surrounding external atmospheric environment via ventilation means (50) mounted on the housing (20) between the said reservoir (30) and the said absorbent matrix (40). The ventilation means (50) may be additionally or alternatively mounted to the matrix housing (45), described below.

The absorbent matrix (40) may be made from any material (400) that is chemically inert with respect to the liquid contents (100), and which readily absorbs the same. Furthermore said material (400) is vapour permeable, allowing the vapour (200) to be released gradually. Thus, said absorbent matrix (40) comprises any suitable material (400) including cotton and/or pressed cardboard.

The said absorbent matrix (40) is held in a suitable matrix housing (45), wherein said matrix housing (45) is releasably or integrally mounted onto the said housing (20), preferably at a lower part (29) thereof. In the preferred embodiment, said matrix housing (45) comprises an open upper side (46), through which said material (400) may be removed and replaced when desired or necessary. Said upper side (46) is defined by a continuous cylindrical or semi-cylindrical vertical side wall (47) sealingly connected at the bottom thereof to a lower wall (48). Suitably-shaped material (400) forming the matrix (40) is placed in the matrix housing (45), and a number of drops of liquid contents (100) is dispensed onto it from the reservoir (30). The amount of liquid (100) dispensed is controlled by the user, and will typically depend on the rate of evaporation of the liquid (100), and the period for which the user desires the vapour (200) to be dispensed into the surrounding environment. Once liquid (100) has been dispensed into the absorbent matrix (40), it will continually evaporate until the absorbent matrix (40) is dry. The vapour (200) leaves the matrix (40) in the matrix housing (45) via the open upper side (46) thereof. The user can at any time repeat the procedure, and may add liquid (100) to the matrix (40), even when the same is still holding liquid (100) that has not yet evaporated. The matrix housing (45), being liquid impermeable, is able to hold a limited supply of liquid, and keep the matrix saturated, if the amount of liquid (100) that the user desires to evaporate is greater than can be held by the absorbent matrix at full saturation.

In one embodiment, the said matrix housing (45) is releasably mounted on said housing (20), and/or the said ventilation means (50) is releasably mounted on said housing, and the absorbent matrix (40) is replaceable.

Ventilation means (50), suitably located on the mid-part (28) of the said housing (20) allows open communication between the open upper side (46) of the matrix housing (45)—and therefore the absorbent matrix (40)—and the external atmospheric environment via ventilation openings (55). In the preferred embodiment, said ventilation means (50) comprises a cylindrical or semi-cylindrical wall (52) of a substantially equal diameter to the matrix housing (45), and is releasably mounted by suitable means to the upper open end of the said matrix housing (45) and/or the said housing (20). Said cylindrical wall (52) thus comprises at least one ventilation opening (55) which allow open communication ultimately between the matrix (40) and the external atmosphere. Said ventilation openings (55) may constitute orifices of any suitable shape, typically circular, or may comprise a grille arrangement. Alternatively, said ventilation means (50) may comprise a cylindrical or semi-cylindrical wall as described, wherein said wall is comprised of a gauze material, preferably made from metal or plastic. Optionally, said ventilation means (50) may further comprise an upper cap part (56) comprising at least one aperture (57) wherein the centre thereof is aligned with the central axis of the outlet (38) of the reservoir (30). Thus, outlet (38) may be located directly above aperture (57), so that on actuation of the nozzle valve (36), liquid (100) will drop, under gravity, through the aperture (57) and onto the absorbent matrix (40). In the preferred embodiment, the outlet (38) of said reservoir (30) extends into said ventilation means (50) through the aperture (57), while the valve (36) may remain above the upper cap part (56), as shown in FIG. 5. Dispensation of said liquid will therefore occur inside the space enclosed by the ventilation means (50) and reduce the risk of spillage during dispensation. Preferably, said outlet (38) is sealingly fitted through said aperture (57). Alternatively, when the valve (36) is indirectly actuated as hereinbefore described, the same may also be located within the ventilation means (50).

Optionally, said ventilation means (50) further comprises means for regulating the size and/or number of the said at least one ventilation opening (55), and/or means for closing said at least one ventilation opening (55). Thus, ventilation means (50) further comprises suitable closure means (60) which enable said ventilation openings (55) to be effectively blocked or closed. Thus, in the event that the matrix (40) still contains liquid (100), release of vapour (200) into the external environment is substantially prevented. Furthermore, insects, dust particles and other pollutants are avoided entry into the matrix (40), particularly when the device (10) is not used for relatively long periods. The possibility of incurring potential damage to said absorbent matrix (40) is also reduced. By way of example, said closure means (60) may comprise a substantially cylindrical or semi-cylindrical cover (62), of internal diameter slightly greater than the external diameter of the ventilation means cylindrical wall (52), overlapping mounted on same, and with freedom to be displaced vertically on same. As shown on FIG. 6(a), cover (62) completely covers the said ventilation openings (55), while FIG. 6(b) shows the cover (62) displaced vertically downwards and over the matrix housing (45), exposing the said ventilation openings (55). Optionally still, closure means (60) may further comprise closure regulating means (65) that enable the ventilation openings (55) to be selectively or gradually blocked, thus enabling the flow rate of vapour (200) to the external environment to be regulated further. With reference to FIG. 6(c), said closure regulating means (65) may comprise a ratchet arrangement, wherein opposing faces (521), or (471), and (621) of the walls (52), or (47), and (62), respectively, comprise similar tooth-like serrations, (65a) and (65b) respectively, which permit movable locking engagement of the cover (62) with the cylindrical wall (52). Other examples of closure means (60) and closure regulating means (65) are known in the art.

In another embodiment, said ventilation means (50) comprises a third cap member (51) which is suitably mounted on top of said matrix housing (45) and/or said housing (20). Said third cap member (51) comprises a substantially horizontal wall (53) with at least one ventilation opening (55), and said absorbent matrix (40) may abut against the lower side of said wall (53). Said at least one ventilation opening (55) may be located directly below said outlet (38), wherein on actuation of the valve (36), liquid (100) is delivered via said opening (55) to the said absorbent matrix (40). Alternatively, the at least one ventilation opening (55) may be located elsewhere on said wall (53), wherein said wall (53) further comprises an aperture (57) directly below said outlet (38) as hereinbefore described. Said outlet (38) may alternatively extend through said aperture (57) and penetrate said absorbent matrix (40) to some depth. This embodiment may further comprise closure regulation means (65) and/or closure means (60). Closure means (60) may comprise a suitably shaped fourth cap member (69) that may be releasably fitted over said wall (53), thereby sealing off said aperture (57) and/or said at least one ventilation opening (55). Alternatively, said closure means may constitute a peelable skin comprising an adhesive surface, wherein said adhesive surface allows said skin to adhere to said wall (53), thereby sealing off said aperture (57) and/or said at least one ventilation opening (55). Alternatively, closure means (60) may comprise one suitably shaped plug member for each ventilation opening (55), wherein each said plug member may be releasably and sealingly plugged into each corresponding ventilation opening (55). Said closure regulation means (65) may comprise a butterfly-valve arrangement for each ventilation opening (55). Alternatively, said fourth cap member (69) may be rotatable over said wall (53), and further comprises at least one opening (67) located on said fourth cap member (69). Said openings (67) are strategically located on said fourth cap member (69) to allow said ventilation openings (55) to be exposed, partially blocked or totally blocked, as said fourth cap member (69) is progressively rotated over said wall (53). Other examples of closure means (60) and closure regulating means (65) are known in the art.

Said ventilation means (50), said closure means (60) and said closure regulating means (65) are preferably made from any suitable material that is chemically and physically inert with respect to the liquid contents (100) and to the said vapour (200).

Figure 9:
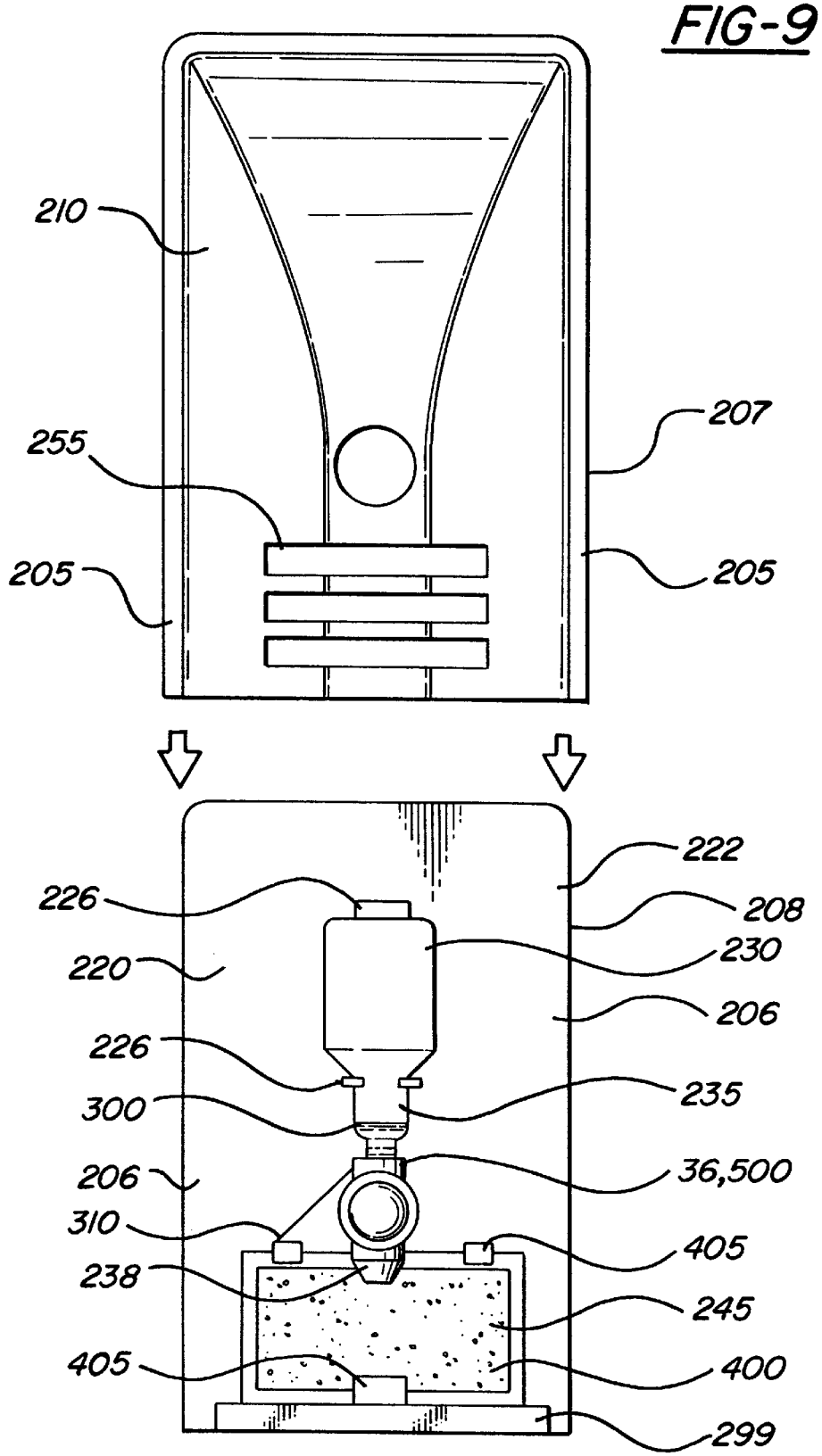
FIG. 9 shows, in partially exploded front view, another embodiment of the invention.
Figure 10:
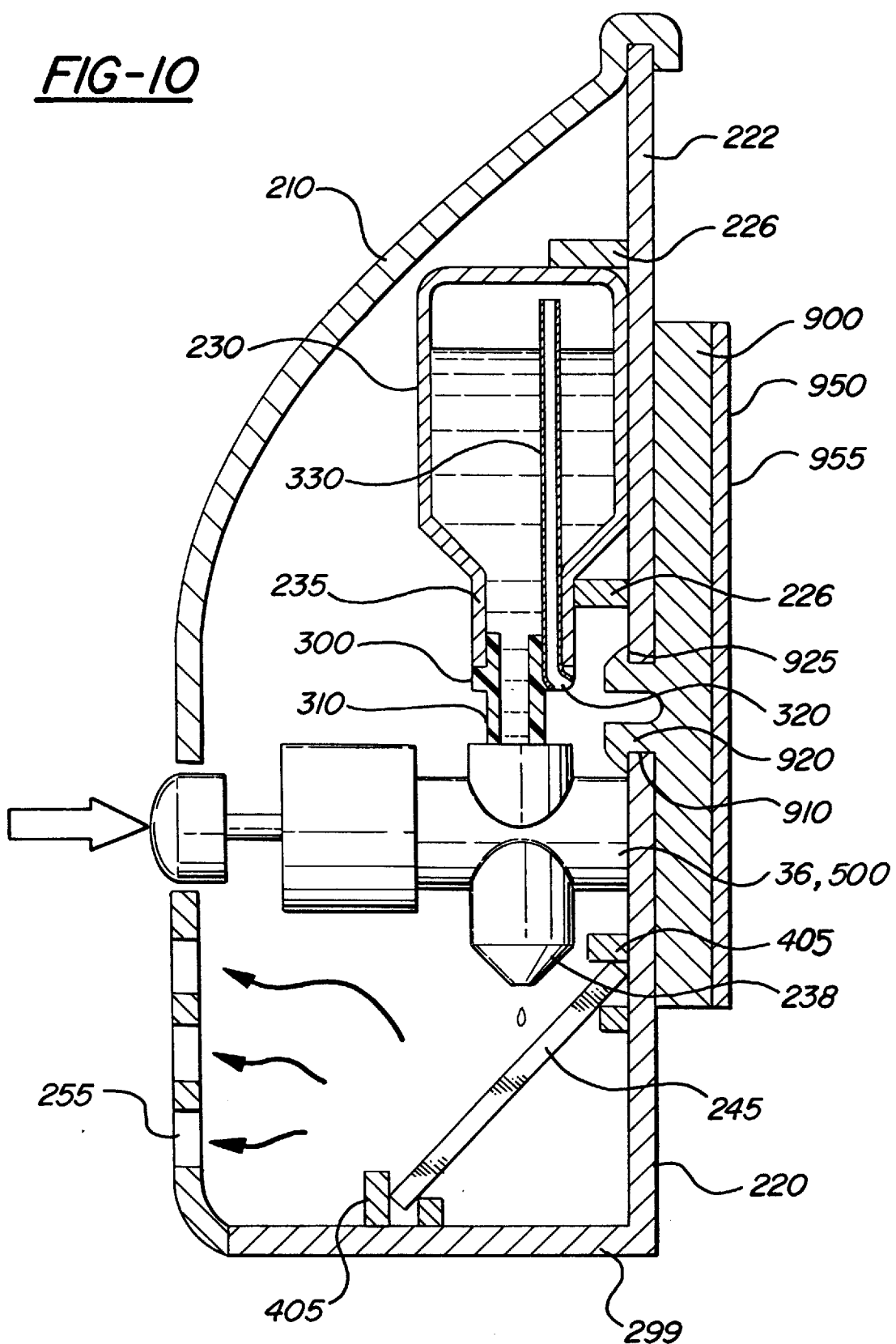
FIG. 10 shows, in side sectional view, the embodiment of FIG. 9.

Another embodiment of the present invention, shown in FIGS. 9 and 10, is particularly suitable for dispensing controlled amounts of highly concentrated volatile liquids, wherein said controlled amounts may only constitute a droplet or a number of droplets of the liquid. A housing member (210) comprises a box construction, open at a lower end and at the back end thereof, and having integral ventilation openings (255). Said ventilation openings (255) may consist, for example, of slots as shown, or alternatively, of any other shape including geometrical cutouts which together may form a decorative mosaic pattern. Said housing member (210) is slidingly engageable onto an L-shaped base part (220) comprising a vertical base part (222) and a horizontal base part (299) by means of complementary rail elements (205) and (206) along corresponding vertical back edges, (207) and (208) respectively, of the housing member (210) and the vertical base part (222). Said housing member (210) and base part (220) may optionally further comprise a latch arrangement or snap-fit arrangement (not shown) to keep the same in a mutually locked position.

Optionally, said vertical base part (222) further comprises a circular aperture (910) through which a circular peg (920) attached to an auxiliary mounting base (900) is inserted. Said mounting base (900) comprises vertical mounting means (950), for example an adhesive strip (955), for mounting same onto any suitable vertical surface. Said peg (920) may comprise several radial slots (not shown), enabling the peg (920) to deform and thus facilitate its insertion into the aperture (910), and further comprises an external abutment (925) which engages the inner surface of said vertical base part (222) in the vicinity of the aperture (910), whereby the peg is retained in place. The vertical base part (222), and therefore the device, is thus rotatable relative to the said mounting base (900) via said peg (920). In this way, replacement of the reservoir (230) is greatly facilitated: once housing member (210) is removed, the L-shaped base part (220) is rotated by 180°, thereby righting the reservoir (230), and enabling its removal and re-attachment to the cap member (300) to be performed with a minimum of spillage of reservoir contents; the L-shaped base part (220) is then rotated by another 180°, inverting the reservoir to its dispensing orientation, followed by replacement of the housing member (210).

An absorbent matrix (245), typically in the form of a rectangular slab or, particularly when the absorbent material (400) is not sufficiently stiff, held by a rectangular frame, is releasably mounted at an angle to the said vertical base part (222) and said horizontal base part (299) and is held in place, by means of suitable stoppers (405), directly below the fluid outlet port (238).

A reservoir (230), typically consisting of a commercially available low-capacity glass bottle, comprises a mouth (235), and is mounted in an inverted position on the said vertical base part (222) by suitable mounting means (226), as hereinbefore described, for example. A cap member (300), sealingly mounted onto said mouth (235), comprises an outlet (310) and an air inlet (320) having a pipe (330) extending into the reservoir (230), wherein open communication is maintained between the external environment and the top of the internal volume of the reservoir (230), enabling air to be drawn into the same to take up the volume of liquid that is dispensed therefrom, as hereinafter described. Advantageously, said cap member (300) is internally profiled to ensure that the reservoir (230) may be fully emptied of contents during the course of normal dispensing operations, and typically, the cap member has an internal substantially funneled profile leading to the outlet (310).

The fluid outlet (310) is sealingly mounted onto said valve mechanism (36), as hereinbefore described, having a fluid outlet port (238).

This invention also relates to a valve, which is novel per se, for controlling the gravitational dispensation of a liquid in droplet form comprising:

(i) a valve casing open at one end thereof and comprising a longitudinal bore, an upper transverse inlet bore having a first diameter and a lower outlet bore generally opposed thereto and having a second diameter, said inlet and outlet bores being in open communication with said longitudinal bore;

(ii) a longitudinal plunger comprising a generally transverse bore having a third diameter, wherein said transverse bore comprises an inlet and an outlet, and wherein said plunger is longitudinally insertable in said casing via said open end and is longitudinally shiftable in, or rotatable within, said casing between an open position, wherein said plunger bore inlet and outlet are respectively aligned with respect to said casing inlet and outlet bores, and a closed position, wherein said plunger bore inlet and outlet are respectively misaligned with respect to said casing inlet and outlet bores; and (iii) an annular plug having a bore of said third diameter and sealingly fitted within said upper boss bore, and protruding into the casing bore to form tangential contact with said plunger;

wherein said valve is characterised in that said third diameter is smaller that said first diameter and said second diameter, and that said third diameter is further correlated to a characteristic droplet size of said liquid, so that in the open position, liquid contained upstream of said plug may be gravitationally dispensed via said plug and plunger bore in discrete droplets into the outlet bore, and further characterised in that in the closed position, the plunger substantially seals the plug core substantially preventing leakage of said liquid therefrom.

Thus, alternatively, said fluid outlet may instead be sealingly mounted onto a droplet-dispensing valve mechanism (500), enabling discrete droplets of fluid to be dispensed via fluid outlet port (238).

Figure 11:
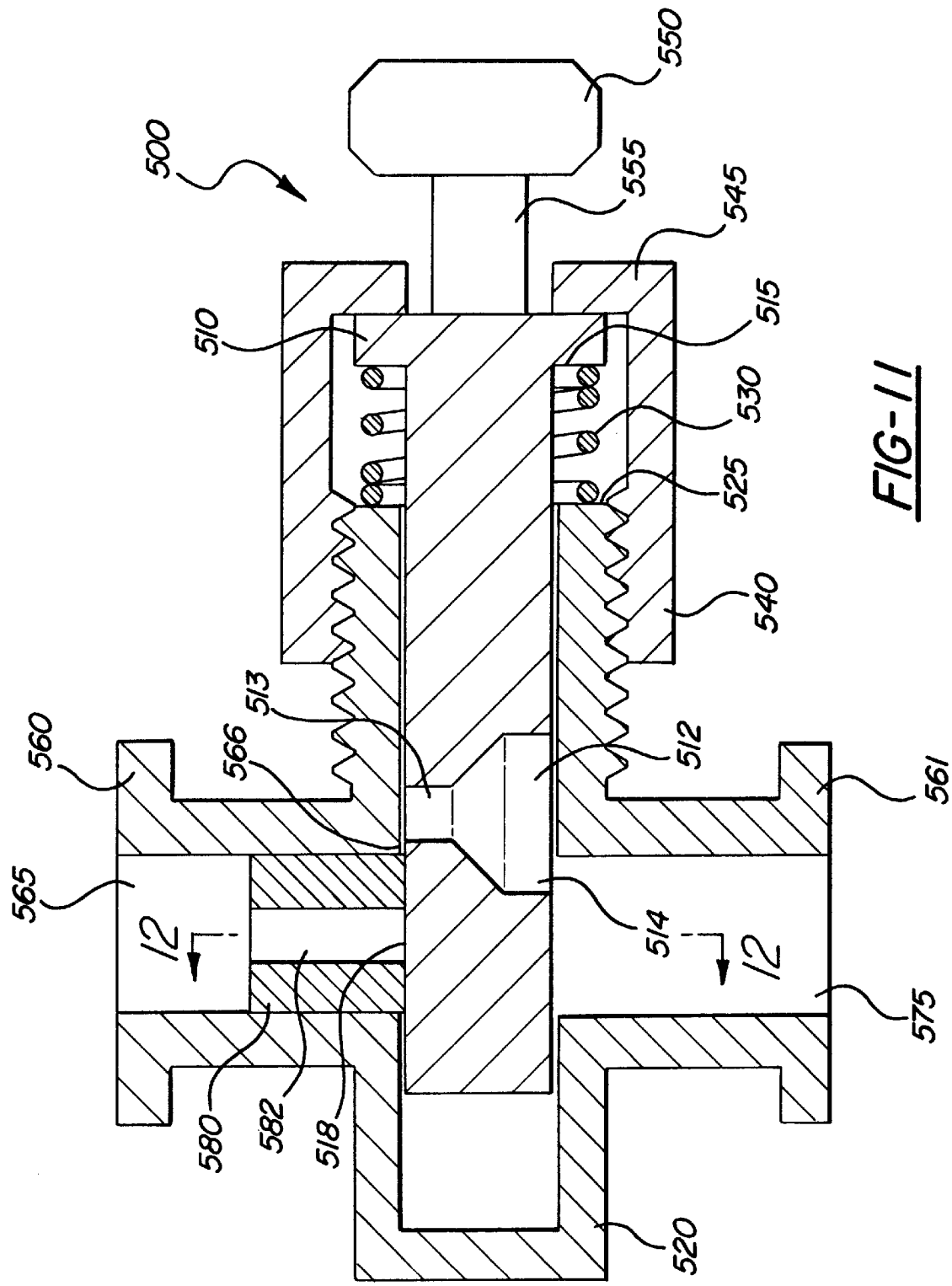
FIG. 11 shows, in side sectional view, a preferred embodiment of the droplet-dispensing valve of the present invention.
Figure 12:
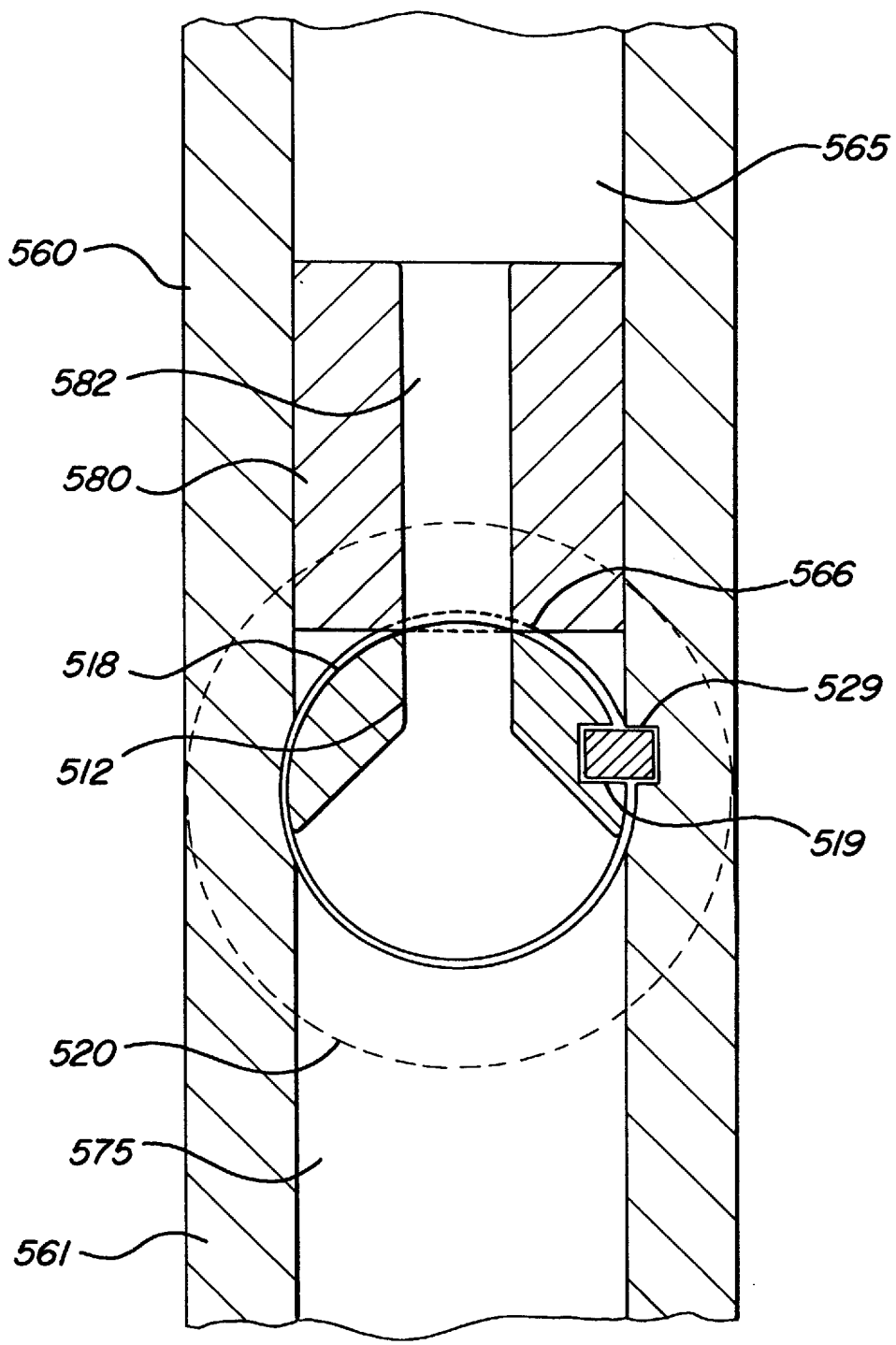
FIG. 12 shows a cross-sectional view of the valve shown in FIG. 11, taken along Y—Y.
Figure 13:
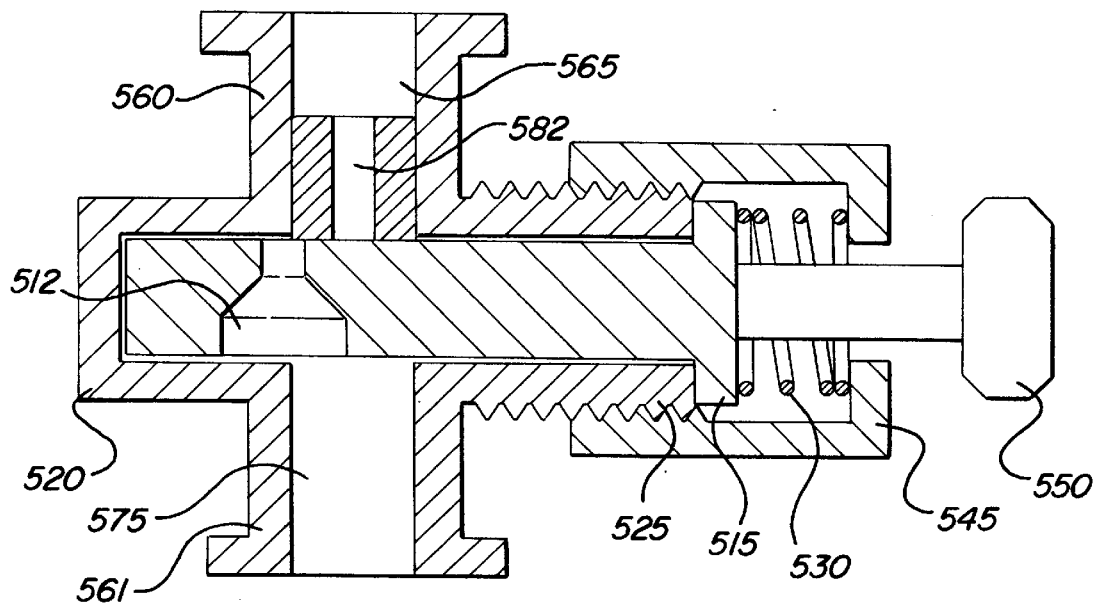
FIG. 13 shows, in side sectional view, another embodiment of the droplet-dispensing valve of the present invention.

Referring to FIGS. 11, 12 and 13, a preferred embodiment of the droplet-dispensing valve mechanism (500) includes a plunger (510) which is axially shiftable within a concentric valve housing (520). The plunger (510) is typically of constant circular cross-section and has a shoulder (515) at one end thereof. A biasing spring (530) abuttable against said shoulder (515) and the mouth (525) of the valve housing (520) maintains the plunger (510) at its extended position abutting the annular shoulder (545) of a cap member (540) which is typically mounted onto the valve housing (520) by the threaded rotation of said cap member (540) onto said valve housing (520), though other mounting means known in the art may also be suitable. The plunger (510) comprises a transverse bore (512), near the enclosed end thereof, and an actuating push button (550) at the free end which projects beyond the annular shoulder (545) by means of a connecting strut (555). Said plunger bore (512) has a small diameter, typically 1 mm, at the upper end (513) thereof, flaring out to a larger diameter at the lower end (514) thereof. The valve housing (520) comprises an upper inlet boss (560) and a lower outlet boss (561), having corresponding co-axial bores (565) and (575) respectively, which are also co-axial with the plunger bore (512) when the plunger (510) is fully retracted into the valve casing (520). Upper boss bore (565) is typically 3 mm diameter, and further comprises a cylindrical plug member (580) having a concentric bore (582), its diameter being correlated to a characteristic droplet size of the liquid being dispensed, typically also 1 mm. Said bore (582) aligns with plunger core (512) when the plunger is fully retracted into the valve casing (520). Said plug member (580) is typically made from a sealing material, such as rubber, and extends away from the opening (566) of the bore (565), establishing tangential contact between the planar annular face of the plug member (580) and the cylindrical surface (518) of the plunger (510). Thus, the plug member bore (582) is sealed against the cylindrical surface (518) until the plunger bore (512) is aligned with it, thereby preventing leakage of fluid from the valve (500). Alternatively, plug member (580) may comprise a cylindrically profiled face complementary to the profile of the cylindrical surface (518) of the plunger. Said plunger (510) and valve casing (520) form a kinematic pair, wherein relative motion is constrained to sliding, thereby ensuring alignment of the plunger core (512) with the upper and lower boss bores (565) and (575), respectively. Thus, for example, the plunger (510) may comprise a keyway (519) and the valve casing comprise a corresponding key (529), or vice versa. Alternatively the strut (555) may have a rectangular cross-section, wherein the annular shoulder (545) has a complementary rectangular orifice to accommodate same.

The small diameter of the plug member bore (582) enables the liquid in the reservoir (230) to be dispensed dropwise, rather than in a steady stream. Thus, when the push button (550) is pressed in, the plunger (510) makes a forward stroke, aligning the plunger bore (512) with the plug member bore (582) and lower boss bore (575). A single drop of liquid is then transferred from the cylindrical member bore (582), via said plunger bore (512), to said outlet boss bore (575), which is sealingly mounted onto said fluid outlet port (238). On release of the push button (550), the spring (530) displaces the plunger in the reverse stroke direction to the original position, and sealing off the plug member bore (582).

Optionally, the spring (530) may be removed, whereby when push button (550) is pressed in, the plunger bore (512) is aligned as before with the plug member bore (582) and lower boss bore (575), and liquid is continuously transferred in a dropwise manner from cylindrical member bore (582), via said plunger bore (512), to said outlet boss bore (575). By pulling the push button (550) to its original closed position, the plug member bore (582) is once again sealed off, terminating dispensation of liquid until the push button (550) is once again pressed in.

An alternative embodiment of the droplet-dispensing valve, with reference to FIG. 13, differs from the described preferred embodiment of the said droplet-dispensing valve in that shoulder (515) abuts the mouth (525) of the valve housing (520), and the spring (530) may then be located between the shoulder (515) and the annular shoulder (545), wherein a pulling action on push-button (550) is required to align the plunger bore (512) with the plug member bore (582) and lower boss bore (575).

Figure 14:
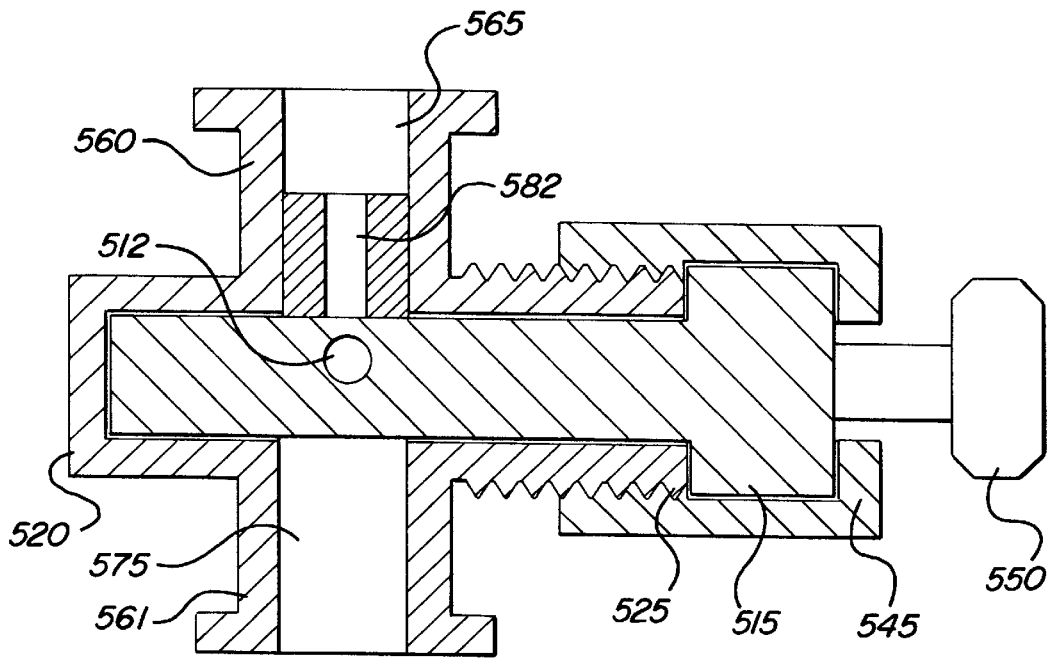
FIG. 14 shows, in side sectional view, another embodiment of the droplet-dispensing valve of the present invention.

An alternative embodiment of the droplet-dispensing valve, with reference to FIG. 14, differs from the described valve embodiments in that shoulder (515) abuts the mouth (525) of the valve housing (520) and also the annular shoulder (545), and further does not comprise said keyway (519) and key (529), so that a kinematic pair with respect to permitting only relative rotational motion is provided. Thus, a rotational action on the push-button (550) is required to align the plunger bore (512) with the plug member bore (582) and lower boss bore (575), and an opposite counter-rotational action similarly mis-alignes the plunger bore (512) with the plug member bore (582) and lower boss bore (575). Optionally, a circumferential stopper (not shown) may be provided to facilitate alignment of the plunger bore (512) with the plug member bore (582) and lower boss bore (575).

Thus, a predetermined amount of fluid (100) may be delivered under gravity onto the absorbent matrix (245) on actuation of valve mechanism (36) or droplet-dispensing valve mechanism (500). As the fluid evaporates from the absorbent matrix (245), the vapour thus formed is released to the external environment via the ventilation openings (255).

Although only a few embodiments have been described in detail in the forgoing description, the present invention is not limited thereto, and is only defined by the scope of the appended claims.

I claim:

1. A device for the controlled dispensation and unattended evaporation of volatile liquids, comprising a housing accommodating:
    (i) a reservoir charged with said volatile liquid and having an outlet at a lower end thereof;
    (ii) valve means suitably mounted on said reservoir for controlling the flow of said volatile liquid through said outlet, wherein said valve means allows a controlled quantity of said volatile liquid comprising discrete droplets to be gravitationally delivered, on demand, to
    (iii) an absorbent matrix supported by a matrix housing, wherein liquid delivered via said outlet is absorbed into said absorbent matrix and dispensed as a vapor to an external environment; via
    (iv) ventilation means comprising at least one ventilation opening in open communication with said absorbent matrix and said external environment.

2. A device according to claim 1 wherein said reservoir is integrally or releasably mounted on said housing.

3. A device according to claim 1, wherein said reservoir may be refillable and farther comprises a releasably mounted cap.

4. A device according to claim 1, wherein the said releasably mounted reservoir is a commercially available container containing said volatile liquid.

5. A device according to claim 1, wherein said matrix housing is releasably mounted on said housing.

6. A device according to claim 1, wherein said reservoir is made from any material that is physically and chemically inert with respect to the contents stored therein.

7. A device according to claim 6 wherein said material is glass.

8. A device according to claim 1, wherein said absorbent matrix comprises any suitable absorbent material including cotton and/or pressed cardboard.

9. A device according claim 1, wherein said matrix housing is releasably mounted on said housing and/or wherein said ventilation means is releasably mounted on said housing, and wherein said absorbent matrix is replaceable.

10. A device according to claim 1, wherein said volatile liquid includes air-freshening preparations, air purifying preparations, perfumed preparations, smoke neutralising preparations, and/or insect repelling preparations.

11. A device according to claim 1 wherein said volatile liquid is derived from natural substances including essential oils and/or plant extracts.

12. A device according to claim 1, wherein said device further comprises means for releasably or permanently attaching said device to a vertical surface.

13. A device according to claim 1, wherein said ventilation means further comprises means for regulating the size and/or number of the said at least one ventilation opening, and/or means for closing said at least one ventilation opening.

14. A device according to claim 1, wherein said device further comprises means for substantially preventing unauthorised use thereof.

15. A device according to claim 1, wherein said valve means comprises:

(i) a valve casing open at one end thereof and comprising a longitudinal bore, an upper transverse inlet bore having a first diameter and a lower outlet bore generally opposed thereto and having a second diameter, said inlet and outlet bores being in open communication with said longitudinal bore;

(ii) a longitudinal plunger comprising a generally transverse bore having a third diameter, wherein said transverse bore comprises an inlet and an outlet, and wherein said plunger is longitudinally insertable in said casing via said open end and is shiftable within said casing between an open position, wherein said plunger bore inlet and outlet are respectively aligned with respect to said casing inlet and outlet bores, and a closed position, wherein said plunger bore inlet and outlet are respectively misaligned with respect to said casing inlet and outlet bores; and (iii) an annular plug having a bore of said third diameter and sealingly fitted within said upper boss bore, and protruding into the casing bore to form tangential contact with said plunger;

wherein said valve means is characterized in that said third diameter is smaller than said first diameter and said second diameter, and that said third diameter is further correlated to a characteristic droplet size of said volatile liquid, so that in the open position, liquid contained upstream of said plug may be gravitationally dispensed via said plug and plunger bore in discrete droplets into the outlet bore and thence to said absorbent matrix, and further characterized in that in the closed position, the plunger substantially seals the plug core substantially preventing leakage of said liquid therefrom.

16. A valve according to claim 15, wherein said plug is made from a pliable sealing material including rubber.

17. A valve according to claim 16, wherein a biasing spring applies a biasing force to maintain said valve in a closed position, requiring that a force be applied against said biasing force to open said valve.

18. A valve for controlling the gravitational dispensation of a liquid in droplet form comprising:

(i) a valve casing open at one end thereof and comprising a longitudinal bore, an upper transverse inlet bore having a first diameter and a lower outlet bore generally opposed thereto and having a second diameter, said inlet and outlet bores being in open communication with said longitudinal bore;

(ii) a longitudinal plunger comprising a generally transverse bore having a third diameter, wherein said transverse bore comprises an inlet and an outlet, and wherein said plunger is longitudinally insertable in said casing via said open end and is shiftable within said casing between an open position, wherein said plunger bore inlet and outlet are respectively aligned with respect to said casing inlet and outlet bores, and a closed position, wherein said plunger bore inlet and outlet are respectively misaligned with respect to said casing inlet and outlet bores; and (iii) an annular plug having a bore of said third diameter and sealingly fitted within said upper boss bore, and protruding into the casing bore to form tangential contact with said plunger;

wherein said valve is characterized in that said third diameter is smaller than said first diameter and said second diameter, and that said third diameter is further correlated to a characteristic droplet size of said liquid, so that in the open position, liquid contained upstream of said plug may be gravitationally dispensed via said plug and plunger bore in discrete droplets into the outlet bore, and further characterized in that in the closed position, the plunger substantially seals the plug core substantially preventing leakage of said liquid therefrom.

19. A valve according to claim 18, wherein said plug is made from a pliable sealing material including rubber.

20. A valve according to claim 19, wherein a biasing spring applies a biasing force to maintain said valve in a closed position, requiring that a force be applied against said biasing force to open said valve.

21. A device according to claim 1, wherein said ventilation means is mounted to at least one of said housing and said matrix housing.

22. A device according to claim 1, wherein said matrix housing is integrally mounted on said housing.

23. A device according to claim 15, wherein said plunger is longitudinally shiftable within said casing between said open and closed positions.

24. A device according to claim 15, wherein said plunger is rotationally shiftable within said casing between said open and closed positions.

25. A device according to claim 18, wherein said plunger is longitudinally shiftable within said casing between said open and closed positions.

26. A device according to claim 18, wherein said plunger is rotationally shiftable within said casing between said open and closed positions.

27. A device for the controlled dispensation and unattended evaporation of a volatile liquid, said device comprising a housing accommodating:

(i) a reservoir charged with said volatile liquid and having an outlet at a lower end thereof;

(ii) a valve suitably mounted on said reservoir to control the flow of said volatile liquid through said outlet, wherein said valve allows a controlled quantity of said volatile liquid comprising discrete droplets to be gravitationally delivered, on demand, to (iii) an absorbent matrix supported by a matrix housing, wherein liquid delivered via said outlet is absorbed into said absorbent matrix and dispensed as a vapor to an external environment; via (iv) a ventilator comprising at least one ventilation opening in open communication with said absorbent matrix and said external environment.

* * * * *

UNITED STATES PATENT AND TRADEMARK OFFICE
CERTIFICATE OF CORRECTION

PATENT NO : 5,810,253
DATED : September 22, 1998
INVENTOR(S) : Nissim Ohayon

It is certified that error appears in the above-identified patent and that said Letters Patent is hereby corrected as shown below:

Column 1, line 6, after "present" delete "ivention" and insert therefor --invention--;

Column 4, line 21, after "smaller" delete "that" and insert therefor --than--.

Column 15, line 11, after "a device according", please insert --to--;

Column 16, line 1, after "discrete droplets into outlet bore and" please insert --hence--.

Signed and Sealed this

Twenty-seventh Day of February, 2001

NICHOLAS P. GODICI

*Attest:*

*Attesting Officer*  *Acting Director of the United States Patent and Trademark Office*